United States Patent [19]

Sifniades et al.

[11] 4,358,618
[45] Nov. 9, 1982

[54] DECOMPOSITION OF CUMENE OXIDATION PRODUCT

[75] Inventors: Stylianos Sifniades, Madison; Allen A. Tunick, Boonton; Fred W. Koff, Long Valley, all of N.J.

[73] Assignee: Allied Corporation, Morris Township, Morris County, N.J.

[21] Appl. No.: 276,233

[22] Filed: Jun. 22, 1981

[51] Int. Cl.$^3$ .................... C07C 45/53; C07C 37/08
[52] U.S. Cl. .................... 568/385; 568/798; 585/435
[58] Field of Search .............. 568/798, 385; 585/435

[56] References Cited

U.S. PATENT DOCUMENTS

| | | | |
|---|---|---|---|
| 2,668,180 | 2/1954 | Boardman | 260/610 |
| 2,757,209 | 7/1956 | Joris | 260/621 |
| 2,761,877 | 9/1956 | Mosnier | 568/798 |
| 3,497,561 | 2/1970 | Gelbein | 568/798 |
| 4,016,213 | 4/1977 | Yeh et al. | 260/621 C |
| 4,207,264 | 6/1980 | Anderson et al. | 568/798 |
| 4,310,712 | 1/1982 | Langley | 568/798 |

OTHER PUBLICATIONS

K. Tsunoda et al., Nippon Kagaku Zasshi, vol. 81, No. 2, p. 310, (1960).
M. S. Kharasch et al., J. Org. Chem., vol. 15, pp. 753-762, (1950).

Primary Examiner—James H. Reamer
Attorney, Agent, or Firm—Alan M. Doernberg; Gerhard H. Fuchs

[57] ABSTRACT

A cumene oxidation product containing cumene hydroperoxide (CHP) and dimethylphenylcarbinol (DMPC) is decomposed with acid catalyst in a first step at mild temperatures that lowers the CHP concentration to about 0.5–5% and converts most of the DMPC to dicumylperoxide (DCP). In a second step at mild temperatures the CHP concentration is lowered below 0.4%. In a third step the DCP is decomposed at a higher temperature for a short time to alpha-methylstyrene (AMS), phenol and acetone, with any remaining DMPC also converted to AMS. The DCP concentration is monitored during the third step, and the reaction is stopped by cooling when about 0.5–5% of the DCP remains undecomposed so as to maximize AMS yield.

8 Claims, 2 Drawing Figures

DECOMPOSITION OF CUMENE OXIDATION PRODUCT

BACKGROUND OF THE INVENTION

Phenol is manufactured via air oxidation of cumene to cumene hydroperoxide (CHP), followed by acid-catalyzed cleavage of the latter to phenol and acetone. CHP decomposition is a very exothermic reaction which is normally carried out on a commercial scale in continuous stirred or back-mixed reactors. In such reactors only a small fraction of CHP is unreacted any given time and the reaction medium consists essentially of the products of decomposition of CHP, i.e., phenol and acetone, plus any solvent (e.g., cumene) and other materials added with CHP to the reactor. During cumene oxidation small amounts of dimethyl phenyl carbinol (DMPC) and acetophenone are also formed. In the presence of acid catalyst, DMPC dehydrates to alpha-methylstyrene (AMS), a useful by-product. Very high yields of AMS can be obtained from pure DMPC, e.g., 98% yield upon dehydration over acidic silica at 300° C. In the presence of phenol, however, and more specifically in phenol/acetone/cumene which is solvent in decomposition of technical CHP/DMPC mixtures, the ultimate AMS yield is normally about 50–60 mol% of the DMPC. Main by-products are AMS dimers and cumylphenol which have no commercial value. Formation of cumylphenol also reduces the phenol yield.

G. G. Joris, U.S. Pat. No. 2,757,209, teaches that the amount of AMS dimers and cumylphenol formed can be substantially reduced by carrying out the reaction in two stages. In the first stage CHP is decomposed in a stirred or back-mixed reactor in the presence of small amounts of sulfur dioxide as catalyst and water as catalyst moderator. Preferred conditions are: temperature 45°–65° C., sulfur dioxide 50–500 ppm, water 2–5 wt%. Under these conditions the CHP concentration in the reaction mixture withdrawn from the reactor is less than 5% but more than 1% by weight. In the second stage, the mixture withdrawn from the first reactor is heated in a second reactor, optionally with additional catalyst, in order to effect the dehydration of DMPC to AMS. This second reactor is either a batch reactor, or a continuous plug-flow reactor. Preferred conditions are: temperature 110°–120° C., reaction time 5–15 min. Care must be taken to stop the high temperature reaction once AMS formation is completed so as to avoid the dimerization of AMS or the reaction of AMS with phenol to form byproducts.

C. Y. Yeh, et al, U.S. Pat. No. 4,016,213, teaches a modification of the above process wherein the back-mix reactor is operated in a manner to avoid the dehydration of DMPC. The mixture withdrawn from the back-mix reactor is immediately treated with base and the DMPC is subsequently recovered from the final distillation wherein crude phenol is the overheads and DMPC is found with acetophenone in the bottoms.

H. Boardman, U.S. Pat. No. 2,668,180, teaches that DMPC and CHP interact in the presence of an acid condensation catalyst to form dicumyl peroxide (DCP). The reaction medium is excess DMPC; examples of catalysts used are p-toluenesulfonic acid, sulfuric acid and boron trifluoride.

Ko. Tsunoda and T. Kato, Nippon Kagaku Zasshi, Volume 81, No. 2, page 310 (1960) studied the reaction of DMPC with CHP in homogeneous benzene/acetic acid solution using perchloric acid as catalyst and also in a two phase benzene/aqueous mixture using sulfuric acid as catalyst. They report that two reactions take place simultaneously: (a) condensation of DMPC with CHP to form DCP, and (b) decomposition of CHP to phenol and acetone.

These last two references indicate that DCP may also be formed during the acid catalyzed decomposition of technical CHP. M. S. Kharasch et al, Journal of Organic Chemistry, Volume 15, page 753 (1950), reported that DCP is decomposed in acetic acid solution in the presence of catalytic amounts of perchloric acid to phenol, acetone and AMS dimer. It is, therefore, possible that DCP is formed during the decomposition of technical CHP and that at least some of the AMS dimers formed during the process originate from subsequent decomposition of DCP.

SUMMARY OF THE INVENTION

The present invention includes a process for decomposing a cumene oxidation product mixture containing cumene hydroperoxide (CHP) and dimethylphenyl carbinol (DMPC) to produce phenol, acetone and alpha-methyl styrene (AMS) with reduced byproduct formation which comprises the steps:

(a) mixing the cumene oxidation product with an acid catalyst in a back-mix reactor in the presence of about 0.4 to about 4.5% water, by weight of reaction mixture, at a temperature between about 50° C. and about 90° C. for a time sufficient to lower the CHP concentration of the back-mix reaction mixture to between about 0.5 and about 5.0 weight % and to convert at least 40% of the DMPC in the cumene oxidation product to dicumylperoxide (DCP);

(b) reacting the back-mix reaction product at between about 50° C. and about 90° C. under plug flow conditions for a time sufficient to produce a second mixture having a CHP concentration no more than about 0.4%; and (c) reacting the second reaction mixture, at a temperature between about 120° and about 150° C. under plug flow conditions for a time sufficient to convert at least 90% of the DCP to AMS, phenol and acetone.

Thus the present invention involves intentionally converting a substantial amount of the DMPC to DCP in step (a) while the CHP concentration remains at least 0.5%, lowering the CHP concentration to below 0.4% under mild conditions in step (b) which will not result in substantial AMS formation, and in step (c), quickly converting the DMPC and DCP to AMS. The DCP concentration during step (c) is preferably monitored, e.g. by gas chromatography, and the reaction is stopped by cooling or neutralizing when 0.5–5% of the DCP remains undecomposed.

DETAILED DESCRIPTION OF THE INVENTION

We have discovered that when technical CHP is decomposed in a stirred or back-mixed reactor in the presence of an acid catalyst, varying amounts of DCP are formed. The amount of DCP formed increases with increasing concentration of CHP in the reaction mixture and it may be as high as 70 mol% of the amount of DMPC present in the CHP feed. DCP is relatively stable under conditions that cause substantial CHP decomposition, but it can be decomposed to yield mainly phenol, acetone and AMS under more forcing conditions, e.g., in the presence of increased acid catalyst concentrations or at higher temperature. We have found that high AMS yields are obtained from DCP in the temperature range 120°-150° C. The same higher temperature conditions that favor formation of AMS from DCP also favor dehydration of DMPC to AMS. It is, therefore, convenient to transform both the DMPC and the DCP present in the reaction mixture resulting from the acid catalyzed decomposition of technical CHP in a stirred or back-mixed reactor by simply heating that mixture to 120°-150° C. for a limited period of time in a plug-flow reactor, optionally with additional acid catalyst. The plug flow reactor generally is composed of a heat exchanger in which the reaction mixture is brought up to the desired temperature, in series with a pipe or baffled tank, in which the reaction is completed. The latter part of the reactor is essentially isothermal. The yield of AMS formed in the reaction increases with time as DCP and the residual DMPC decompose, until it reaches a maximum and then decreases as AMS reacts further to form AMS dimers and cumylphenol. The optimum reaction time depends on the temperature and the concentrations of acid catalyst and water present in the mixture. Generally, shorter times are required at higher temperatures and in the presence of higher concentrations of acid and lower concentrations of water.

Figure 2:
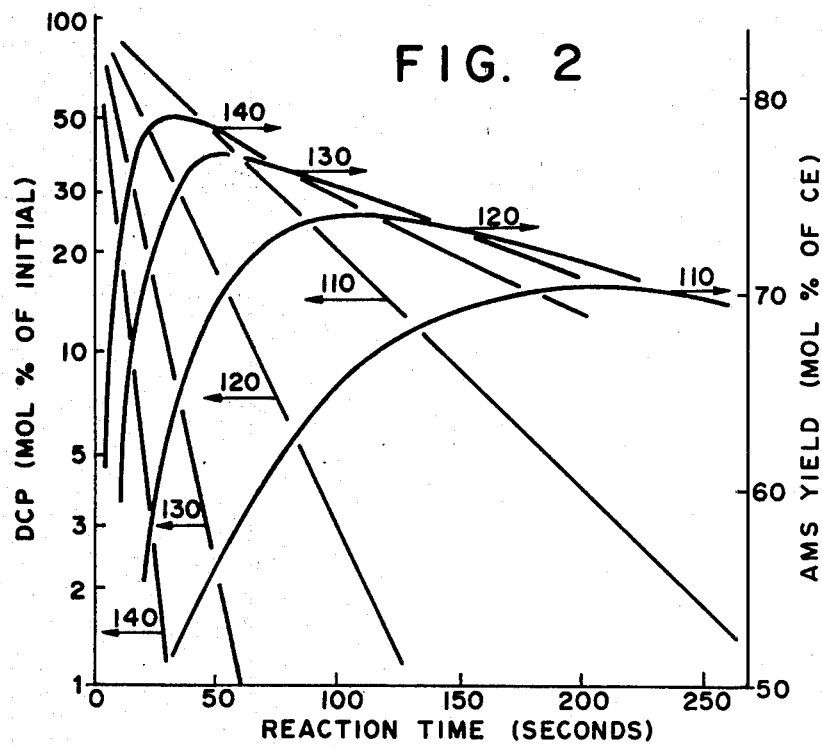

We have found that an excellent way of locating optimum reaction conditions in the plug flow reactor is by monitoring the DCP concentration. The attached FIG. 2 shows the yield of AMS produced and the percentage of DCP left unreacted by heating a typical feedtock at various temperatures (°C. indicated by numbers over arrows) for various periods of time in an isothermal plug-flow reactor. This particular feedstock was produced by decomposing technical CHP (83 wt% in cumene, containing also 3.0 wt% DMPC, 0.4 wt% acetophenone and 0.2 wt% DCP) in a back-mix reactor with residence time 28 min, at 75° C., in the presence of 75 ppm sulfuric acid and 1 wt% added water. The reaction mixture contained 0.93 wt% CHP, 0.69 wt% DMPC, 0.92 wt% AMS, 2.40 wt% DCP and small amounts of AMS dimer, cumylphenol and cumylphenyl ether. Plots similar to those shown in the figure were produced starting from several other feedstock compositions. These plots have two common features:

(a) DCP disappearance is linear on a logarithmic scale, i.e. it follows first order kinetics, under all conditions of practical interest, and (b) The maximum AMS yield is obtained when the remaining DCP concentration is between about 0.5% and about 5% of the DCP concentration charged into the isothermal plug flow reactor.

DCP concentration may be conveniently determined by gas chromatography, liquid chromatography or iodometric titration. Since the DCP concentration at the plug flow reactor exit is relatively low and thus subject to large analytical errors at the DCP conversion desired, it may be more convenient to measure DCP at an intermediate point in the reactor. Because of the linearity of DCP disappearance on a logarithmic scale, the DCP concentration at the reactor exit may be found by extrapolation.

In order to effect substantial transformation of DMPC to DCP, it is necessary to have between 0.5% and 5% CHP, and preferable to have between about 0.8 and about 2% CHP, all by weight, present in the reaction mixture resulting from the decomposition of technical CHP in a stirred reactor; i.e., step (a). The percentage of unreacted CHP can be adjusted by employing the appropriate combination of acid catalyst concentration, reaction temperature, water concentration and residence time in the reactor. The choice of particular combinations of these elements should be easily determinable by routine experimentation. Thus, in addition to sulfur dioxide, various strong stable mineral acids such as sulfuric acid, perchloric acid and the like may be used; or Lewis acids such as boron trifluoride or aluminum chloride may be used; or organic acids such as toluene sulfonic acid may be used. Typical acid levels are between 30 and 400 ppm (0.003-0.04%). Water is desirably added to the back-mix reactor in addition to that formed by the desired reaction of DMPC with CHP to form DCP, by other condensation of DMPC or by the dehydration of DMPC to form AMS. The preferred water concentration present in step (a) is between 0.8 and 1.5% by weight.

The water present from condensation and decomposition of DMPC will be between 0.3 and 0.7% when DMPC is about 3-7% of the oxidation product and about 70-80% of the DMPC is either condensed or dehydrated in the first step. The water level desired for the first step, 0.4 to 4.5%, preferably 0.8 to 1.5%, may be achieved by the water formed from DMPC or may require additional water.

The temperature for step (a) is in the range of 50°-90° C.; preferably 60°-80° C. Below 50° C. removal of the heat of reaction becomes inefficient; above 90° C. the yield of phenol and acetone produced from CHP is significantly diminished. Residence time in the reactor depends on the temperature and acid and water content of the reaction mixture. A typical combination is 70° C., 70 ppm sulfuric acid catalyst, 1% water added, 20 min residence time. Under these conditions the reaction product contains 0.5-5 wt% CHP; some of the DMPC remains unreacted, some is converted to AMS and a large portion is converted to DCP. Only minor amounts of AMS dimers and cumylphenol are formed.

The product of this reactor may be subsequently heated at a higher temperature in a second, plug-flow reactor. This treatment results in the decomposition of residual CHP to phenol and acetone and also in the decomposition of DCP to phenol, acetone and AMS and of DMPC to AMS.

We have also discovered, however, that the acid-catalyzed decomposition of CHP to phenol and acetone proceeds in high yield at temperatures lower than 90° C. At higher temperatures, increasing amounts of DMPC-related by-products are formed. To the extent that unreacted CHP is present in the reaction product of the first reactor and it is decomposed at elevated temperatures in the second reactor, small but significant yield losses of phenol and acetone are incurred (as indicated below in the discussion in the Examples 1-5). We have discovered that these losses can be avoided by placing a third reactor between the two already mentioned. This reactor is plug-flow and is maintained at a temperature which is roughly equal to that of the first reactor. Residence time may be a few minutes. Due to the short residence time required, this reactor may simply be a pipe connecting the other two reactors. Residual CHP is substantially decomposed in this reactor, to below 0.4% and preferably below 0.2%, whereas DCP and DMPC are essentially unaffected. The product from this reactor can then be sent downstream for decomposition of DCP and DMPC at elevated temperatures.

Figure 1:
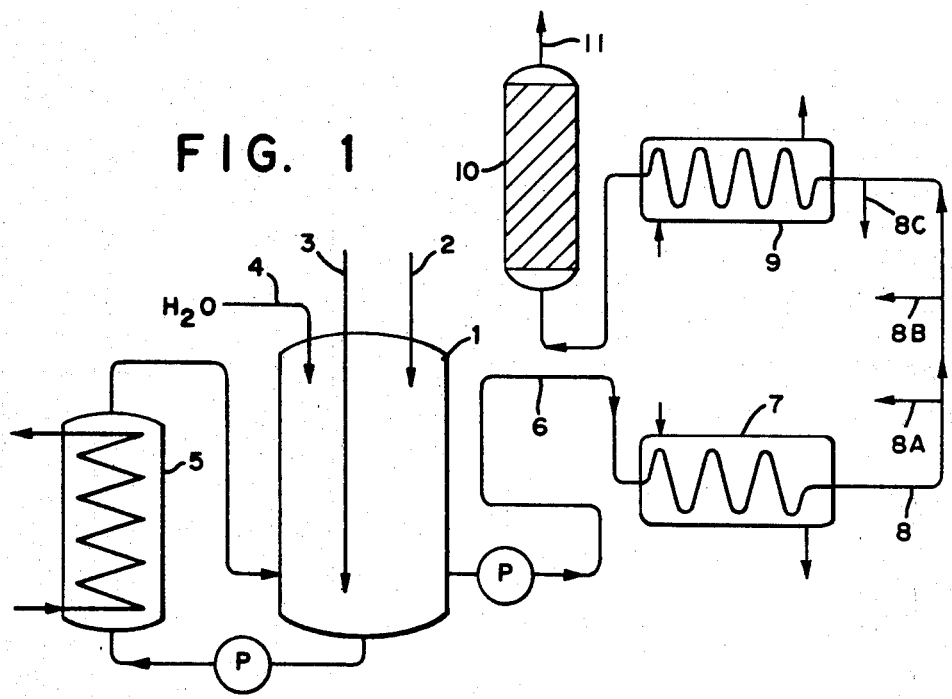

The invention can be illustrated by reference to FIG. 1 which can be compared to the Figure of U.S. Pat. No. 2,757,209. Step (a) is performed in backmix reactor 1 at between 50° C. and 90° C. under conditions establishing a residence time of 5-120 min. Technical CHP, acid catalyst and water are introduced to the reactor through inlets 2, 3 and 4 respectively. The desired temperature is maintained by means of circulation through cooler 5. Due to the strong exothermicity of CHP decomposition, the minimum residence time in reactor 1, which includes time spent in cooler 5 is determined by the design of the cooler, and the nature of cooling fluid. A practical lower limit of approximately 5 min is imposed if the coolant is water. Lower residence time may be achieved if a refrigeration system is employed but this serves no useful purpose. The upper limit of residence time depends on the temperature, the acid content and the water content of the reaction mixture. A residence time of approximately 120 min may be considered as the upper limit. Preferred residence time is between 10 and 60 min.

The product from reactor 1 is next pumped through a piece of tube 6 to heater 7. Step (b) of the reaction is carried out in tube 6 which has sufficient capacity to provide a residence time between 0.1 and 10 min. The temperature in tube 6 is approximately the same as in 1. No means for cooling is provided, because the only significant reaction taking place in this step is decomposition of residual CHP which has already been reduced to 0.5-5% level in step (a). In heater 7 the product is heated to 120°-150° C. and then is pumped to cooler 9 through pipe 8. The total residence time in heater 7 and pipe 8 is sufficient to cause decomposition of DCP and dehydration of DMPC to AMS as well as complete decomposition of any residual CHP. Best AMS yields are obtained if the residence time in heater 7 is relatively short (e.g. under 30 seconds) compared to that in pipe 8 (at least 30 additional seconds), because in that way most of the DMPC dehydrates at the higher temperature regime which favors AMS formation. Pipe 8 is fitted with sampling ports at the entrance 8A, at an intermediate point 8B and at the exit 8C, for monitoring DCP concentration. At the cooler 9, the reaction product is cooled to 30°-50° C. and then sent to an anion exchange resin bed, 10, in order to neutralize the acid catalyst. The neutralized product is then sent to a distillation train for fractionation and recovery of the various components.

EXAMPLES 1-5; DECOMPOSITION OF PURE CHP 0.8 mL of a mixture composed of 53 wt% phenol, 32 wt% acetone and 15 wt% cumene was mixed with 0.004 mL of 2% aqueous sulfuric acid. The resulting mixture contained 0.5% water and 100 ppm acid. It was placed in a 2 mL sealed reaction vessel equipped with a thermometer and a magnetic stirrer. The mixture was placed in an oil bath and heated to 70° C., then 0.75 mL of pure CHP was introduced by a syringe pump through a silicon rubber septum within 7 min. The temperature was maintained at 70° C. during the CHP addition and for an additional 1 min afterwards. Then the reaction mixture was cooled and analyzed by gas chromatography for phenol, AMS, DMPC, AMS dimers, cumylphenol, cumylphenyl ether and acetophenone. All components other than phenol represent undesirable decomposition of CHP (since there was no DMPC initially present). For brevity, AMS, DMPC, AMS dimers, cumylphenol and cumylphenyl ether were added together on an equivalent basis and reported as "carbinol equivalents produced per mol phenol produced." Acetophenone was reported separately because its formation does not involve the intermediacy of DMPC. The experiment was repeated at various temperatures and the results were summarized in Table I. It is clear from the data in Table I that as the temperature of CHP decomposition increases the amount of carbinol equivalents and acetophenone produced also increases. Yield loss of phenol due to these by-products amounts to 0.7 mol% at 90° C. and becomes very significant at higher temperatures. It should be realized that, if DMPC were also originally present, the carbinol equivalents from CHP shown in Table I would be additional to the carbinol equivalents from DMPC.

TABLE I

| | | Acid Catalyzed Decomposition of Pure CHP[a] | | |
|---|---|---|---|---|
| Example | Temperature °C. | By-products (mol/mol phenol) × 100 | | |
| | | Carbinol Equivalent | Acetophenone | Total |
| 1 | 70 | 0.36 | 0.06 | 0.42 |
| 2 | 90 | 0.61 | 0.06 | 0.70 |
| 3 | 110 | 1.24 | 0.15 | 1.49 |
| 4 | 122 | 2.19 | 0.25 | 2.44 |
| 5 | 146 | 5.04 | 0.69 | 5.75 |

[a]In phenol/acetone/cumene solution containing initially 0.5 wt % water and 100 ppm sulfuric acid.

EXAMPLES 6-8: DEHYDRATION OF DMPC

A stock solution containing 6 wt% DMPC, 15 wt% cumene and 50 ppm sulfuric acid with the balance composed of equimolar phenol and acetone was distributed among several melting point capillary tubes which were subsequently sealed and heated for various lengths of time in a stirred oil bath. The tubes were then quickly cooled by immersion in an ice bath and the contents were analyzed by gas chromatography. The amount of AMS formed increased with time up to a maximum yield and then declined as increased amounts of AMS dimers and cumylphenol were formed. Table II records the maximum AMS yield obtained at each temperature, as well as the heating time required to reach that yield. It is clear from the data of Table II that the best yields of AMS were obtained at temperatures over 90° C., e.g., 120° and 130° C.

TABLE II

| | Acid Catalyzed Dehydration of DMPC[a] | | |
|---|---|---|---|
| Example | Temperature °C. | Max. AMS mol % | Time to Max AMS min |
| 6 | 80 | 68 | 15 |
| 7 | 120 | 86 | 1.5 |
| 8 | 130 | 87 | 1.0 |

[a]In phenol/acetone/cumene containing 50 ppm sulfuric acid

When examples 1 to 8 are considered together, it is evident that, given a mixture of CHP and carbinol, it is not possible to obtain highest yields of phenol from CHP and AMS from carbinol at a single temperature because the first transformation gives best yields at temperatures below 90° C. whereas the second gives best yields at temperatures higher than 90° C.

EXAMPLES 9-12: ACID-CATALYZED DECOMPOSITION OF TECHNICAL CHP

Technical CHP, 83 wt%, also containing 3.2 wt% carbinol and 0.4 wt.% acetophenone with the balance being cumene, was pumped into a stirred vessel maintained at 50° C. Simultaneously, a 1% solution of sulfuric acid in phenol was pumped into the vessel at a rate sufficient to maintain a concentration of 50 ppm sulfuric acid in the reaction mixture. Reaction product was continuously withdrawn from the vessel so that the amount of mixture in the vessel remained constant. The residence time of the reaction mixture in the vessel was 17 min. After two hours of continuous operation, the reaction product was analyzed by gas chromatography and found to contain 1% CHP, 0.4% acetophenone and 3.4% total carbinol equivalent. The latter is defined as the sum of all products which can be formed by reactions of DMPC reported as DMPC in wt%. The carbinol equivalent was composed of the following components (as equivalent % of total carbinol equivalent): AMS 18.0, DMPC 15.8, AMS dimers 10.0, DCP 46.5, cumylphenol 9.5, cumylphenyl ether 0.7.

Other examples are summarized in Table II.

These examples show that decomposition of CHP under mild conditions that allow a significant amount of CHP to remain unreacted result in substantial transformation of DMPC to DCP. On the other hand, if the decomposition conditions are such that very little CHP remains unreacted, no significant amount of DCP is formed. Thus in comparative example 12, in which 0.1 wt% CHP remained in the reaction product, only 6.0 mol% of the DMPC-derived products was DCP; moreover, a larger portion of the DMPC was converted to AMS dimers and cumylphenol in this example.

TABLE III

Acid Catalyzed Decomposition of Technical CHP[a]

| | Examples | | | |
|---|---|---|---|---|
| | 9 | 10 | 11 | 12 |
| Temperature, °C. | 50 | 60 | 75 | 75 |
| Time, min | 17 | 13 | 13 | 30 |
| H$_2$SO$_4$, ppm | 50 | 50 | 50 | 75 |
| H$_2$O added, wt % | — | 0.5 | 1.0 | — |
| Acetophenone, wt % | 0.4 | 0.4 | 0.4 | 0.4 |
| CHP, wt % | 1.0 | 0.9 | 1.2 | 0.1 |
| Total CE,[b] wt % | 3.4 | 3.4 | 3.4 | 3.6 |
| AMS, mol % of CE[b] | 18.0 | 8.7 | 22.7 | 51.7 |
| DMPC, mol % of CE[b] | 15.8 | 21.6 | 19.7 | 8.3 |
| CPE,[c] mol % of CE[b] | 0.7 | 1.8 | 1.6 | 0.9 |
| AMS Dimers, mol % of CE[b] | 10.0 | 0.5 | 3.8 | 19.9 |
| DCP, mol % of CE[b] | 46.5 | 65.2 | 47.7 | 6.0 |
| Cumylphenol, mol % of CE[b] | 9.5 | 2.2 | 4.6 | 13.1 |

[a]Initial composition: 83 wt % CHP, 3.2 wt % DMPC, 0.4 wt % acetophenone, balance cumene.
[b]CE = carbinol equivalent
[c]CPE = Cumylphenyl ether

EXAMPLES 13–17: ACID-CATALYZED COMPOSITION OF DCP

A stock solution containing 6 wt% DCP, 15 wt% cumene, 1 wt% water and 50 ppm sulfuric acid with the balance composed of equimolar phenol and acetone was distributed among several melting point capillary tubes which were subsequently sealed and heated for various lengths of time in a stirred oil bath. The tubes were then quickly cooled by immersion in an ice bath and the contents were analyzed by gas chromatography. The amount of AMS formed increased with time up to a maximum yield and then declined as increased amounts of AMS dimers and cumylphenol were formed. Table IV records the maximum AMS yield obtained at each temperature as well as the heating time required to reach that yield. It is clear from the data of Table IV that best yields of AMS are obtained at temperatures over 100° C., e.g., 120° to 150° C.

TABLE IV

Acid Catalyzed Decomposition of DCP

| Example | Temperature °C. | Max. AMS mol % | Time to Max AMS min |
|---|---|---|---|
| 13 | 84 | 68 | 16 |
| 14 | 120 | 82 | 6 |
| 15 | 130 | 88 | 4 |
| 16 | 140 | 89 | 3 |
| 17 | 150 | 90 | 1.5 |

EXAMPLE 18

Technical 83 wt% CHP, also containing 3.4 wt% DMPC, 0.4 wt% acetophenone and 0.3 wt% DCP was pumped at the rate of 2 mL/min into a stirred glass vessel of 32 mL holdup capacity. A 0.49 wt% aqueous solution of sulfuric acid was also pumped into the vessel at the rate of 0.02 mL/min. Thus the resulting reaction mixture contained 1% added water and 49 ppm sulfuric acid; residence time was 16 min. Temperature in the vessel was maintained at 75° C. The reactor effluent contained 2.7 wt% CHP, 0.72 wt% DMPC, 0.4 wt% acetophenone, 4.2 wt% DCP, 0.47 wt% AMS and minor amounts of cumylphenyl ether, AMS dimers and cumylphenol. The reactor effluent was fed through a 150 cm long coiled polytetrafluoroethylene tube immersed in a bath at 75° C. Residence time was 2.6 min. The effluent from the tube contained 0.14% CHP; the other components remained relatively unchanged. The tube effluent was next fed through a coiled 2.2 mm inside diameter stainless steel tube immersed in a bath at 130° C. Residence time was 1.5 min. The effluent was cooled by passage through a coiled 2.2 mm inside diameter stainless steel tube immersed in cold water. The final product contained 2.64 wt% AMS, 0.4 wt% acetophenone, 0.23 wt% DMPC, 0.1 wt% DCP, 0.16 wt% AMS dimers and 0.33% cumylphenol; the balance of the other components analyzed by gas chromatography was phenol, acetone and cumene. Short path distillation of 100 g of the final product at 110° C. and 2.67 kPa (20 mm mercury) left a residue of 1.60 g.

EXAMPLE 19 (COMPARATIVE)

The experiment of Example 18 was repeated with the following modifications: no water was added to the reactor and the polytetrafluoroethylene tube was shortened to 25 cm and maintained at room temperature; residence in the 2.2 mm inside diameter stainless steel tube was 1 min and the temperature was 115° C. The stirred reactor effluent contained 0.10 wt% CHP, 0.4 wt% acetophenone, 0.34 wt% DMPC, 1.43 wt% AMS, 0.91 wt% DCP, 0.51 wt% AMS dimers and 0.4 wt% cumylphenol. The final product contained in 2.02 wt% AMS, 0.4 wt% acetophenone, 0.16 wt% DMPC, 0.60 wt% AMS dimers and 0.78 wt% cumylphenol; the balance of the components analyzed by gas chromatography was phenol, acetone and cumene. Short path distillation of 100 g of final product at 110° C. and 2.67 kPa left a residue of 2.63 g.

GAS CHROMATOGRAPHY ANALYSIS OF CHP DECOMPOSITION MIXTURE

A 2 ft. (61 cm)×2 mm inside diameter Pyrex column packed with 3% QF-1 and 3% OV-17 on 80–100 mesh high performance Chromosorb W was used. The column packing was obtained from Applied Science Laboratories Inc. The column was held at 50° C. for 1 min., then heated at 5° C./min. to 180° C. and held at 180° C. for 3 min. Injection temperature was 150° C. Helium was used as carrier gas at 40 mL/min. Elution times were as follows (in min): cumene, 1.6; AMS, 2.3; phenol, 3–5; DMPC, 5.2; acetophenone, 5.7; CHP, 7.6; hexamethyl benzene (as internal standard), 11.9; cumylphenyl ether, 16.1; AMS dimers, four peaks of area ratio equal to 0.05/0.20/1.00/0.23, correspondingly at 17.6, 18.6, 19.5 and 20.2; DCP, 20.2; cumylphenol, 22.6. In determining the amount of DCP, a correction was applied for contribution of AMS dimers to that peak due to the overlap of DCP and the last dimer peaks. DCP determination was quite reliable down to 0.1 wt% DCP.

What is claimed is:

1. A process of decomposing a cumene oxidation product mixture containing cumene hydroperoxide (CHP) and dimethylphenylcarbinol (DMPC) to produce phenol, acetone and alpha-methyl styrene (AMS) with reduced by-product formation which comprises the steps:
   (a) mixing the cumene oxidation product with an acid catalyst in a back-mix reactor in the presence of about 0.4 to about 4.5% water, by weight of reaction mixture, at a temperature between about 50° C. and about 90° C. for a time sufficient to lower the CHP concentration of the back-mix reaction mixture to between about 0.5 and about 5.0 weight % and to convert at least 40% of the DMPC in the cumene oxidation product to dicumylperoxide (DCP);
   (b) reacting the back-mix reaction mixture at between about 50° C. and about 90° C. under plug flow conditions for a time sufficient to produce a second mixture having a CHP concentration no more than about 0.4; and
   (c) reacting the second reaction mixture at a temperature between about 120° and about 150° C. under plug flow conditions for a time sufficient to convert at least 90% of the DCP to AMS, phenol and acetone.

2. The process of claim 1 wherein the back-mix reaction mixture contains about 0.8 to 1.5% water and about 30 to about 100 ppm sulfur dioxide or sulfuric acid and is at between about 60° and about 80° C.

3. The process of claim 1 wherein the time for step b is sufficient to lower the CHP concentration to no more than about 0.2%.

4. The process of claim 1 wherein the product from step b is heated to the temperature of step c in under 30 seconds and then maintained at that temperature for at least 30 additional seconds.

5. The process of claim 1 further comprising the step:
   (d) measuring the DCP concentration during said step c and cooling the reaction mixture to below 100° C. to stop the reaction when about 0.5 to about 5% of the DCP in the second mixture remains unconverted.

6. A method for the production of alpha-methylstyrene in a phenol-acetone-cumene solution which comprises the steps:
   (a) heating a first mixture comprising phenol, acetone, cumene and dicumyl peroxide to a temperature between about 120° C. and about 150° C. under plug flow conditions,
   (b) measuring the dicumyl peroxide concentration,
   (c) cooling the reaction mass to below 100° C. to stop the reaction and reduce by-product formation from alpha-methylstyrene when the dicumyl peroxide concentration is between about 0.5 and about 5.0% of the dicumyl peroxide concentration of said first mixture.

7. The method of claim 6 wherein said measuring step b comprises analyzing an aliquot of the reaction mass by gas chromatography and measuring the area of the dicumyl peroxide peak.

8. The method of claim 6 or 7 wherein said first mixture is heated to said temperature in under 30 seconds and then maintained at said temperature for at least 30 additional seconds.

* * * * *